United States Patent [19]

McCarthy et al.

[11] Patent Number: 5,508,393
[45] Date of Patent: Apr. 16, 1996

[54] PROCESS FOR THE PREPARATION OF RIBONUCLEOTIDE REDUCTASE INHIBITORS

[75] Inventors: James R. McCarthy; Donald P. Matthews, both of West Chester; Jeffrey S. Sabol, Loveland, all of Ohio; James R. McConnell; Richard E. Donaldson, both of Midland, Mich.; Robert Duquid, Richmond, Va.

[73] Assignee: Hoeschst Marion Roussel, Inc., Cincinnati, Ohio

[21] Appl. No.: 439,536

[22] Filed: May 11, 1995

Related U.S. Application Data

[63] Continuation of Ser. No. 178,952, Jan. 7, 1994, abandoned, which is a continuation-in-part of Ser. No. 31,012, Mar. 26, 1993, abandoned, which is a continuation-in-part of Ser. No. 881,978, May 12, 1992, abandoned.

[51] Int. Cl.$^6$ .................................................. C07H 19/06
[52] U.S. Cl. .................. 536/28.5; 536/28.51; 536/28.52; 544/245; 544/321; 544/317
[58] Field of Search ................. 536/28.1, 28.4, 536/28.5, 28.51, 28.52; 544/245, 310, 321

[56] References Cited

U.S. PATENT DOCUMENTS 5,047,520   9/1991   Matsuda et al. .................. 536/28.5

FOREIGN PATENT DOCUMENTS 0365849   6/1990   European Pat. Off. .
0372268   6/1990   European Pat. Off. .
0398230   11/1990  European Pat. Off. .
0443471   8/1991   European Pat. Off. .

OTHER PUBLICATIONS

McCarthy, et al., Tetrahedron Letters 31(38):5449–5452 (1990).

Sabol, et al., Tetrahedron Letters 33(22):3101–3104 (1992).

McCarthy, et al., J. of The American Chem. Society, 113 (19): 7439–7440 (Sep. 11, 1991).

Takenuki, et al., J. Med. Chem. 31:1064–1066 (1988).

Matsuda, et al., Chem. Pharm. Bull. 36(3):945–953 (May 24, 1988).

Markiewicz et al., Tetrahedron Letters, vol. 29, No. 13, pp. 1561–1564, (1988).

*Primary Examiner*—Douglas W. Robinson
*Assistant Examiner*—James Oliver Wilson
*Attorney, Agent, or Firm*—Nelsen L. Lentz

[57] ABSTRACT

The present invention is directed toward a novel process of preparing 2'-exocyclic vinylfluoride derivatives of cytidine analogues for use as ribonucleotide reductase inhibitors. The novel process of the present invention utilizes a cytidine derivative as the required starting material and provides the ribonucleotide reductase inhibitor in a more efficient five step reaction sequence. The present invention further provides the ribonucleotide reductase inhibitor in a four step reaction sequence and results in an overall yield of greater than 35%.

3 Claims, No Drawings

PROCESS FOR THE PREPARATION OF RIBONUCLEOTIDE REDUCTASE INHIBITORS

CROSS-REFERENCE TO RELATED APPLICATION

This is a continuation of application Ser. No. 08/178,952, filed Jan. 7, 1994, now abandoned, which is a continuation in part of application Ser. No. 08/031,012 filed Mar. 26, 1993 now abandoned which is a continuation in part of application Ser. No. 07/881,978 filed May 12, 1992 now abandoned which is herein incorporated by reference.

BACKGROUND OF THE INVENTION

The present invention relates to a novel process for the preparation of ribonucleotide reductase inhibitors. The target compounds of the novel process described in this application are disclosed by McCarthy et al. in European Patent Application Publication No. 0 372 268 published Jun. 13, 1990. The previous synthesis of these compounds involved a seven step reaction sequence in which a uridine derivative was the required starting material. The uridine derivative was converted to the known ketone intermediate of structure (A)

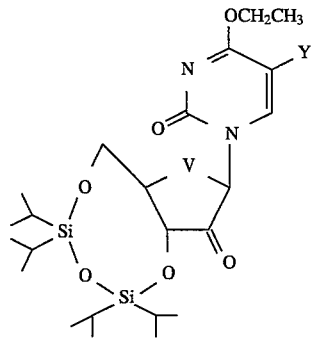

wherein V is oxy or methylene and Y is hydrogen, $C_1$-$C_4$ alkyl or $C_1$-$C_4$ alkoxy, following generally the procedure of Matsuda et al. [*Chem. Pharm. Bull.* 1988, 36(3), 945] in an eight step process from commercially available starting material that was labor intensive and involved multiple chromatographies. This intermediate was then subjected to olefination at the 2'-carbonyl to produce the exocyclic fluorovinyl sulfone followed by stannylation to provide the exocyclic (fluorovinyl) stannane. In the final step this compound was destannylated and the 3', 5'-hydrolysis were deprotected to provide the desired ribonucleotide reductase inhibitor in low yield.

The novel process of the present invention utilizes a cytidine derivative as the required starting material and provides the ribonucleotide reductase inhibitor in a more efficient five step reaction sequence. The process is more efficient than the process of McCarthy et al. in that it requires fewer chromatographies and results in an overall yield of greater than 25% for the five steps.

The present invention further provides the ribonucleotide reductase inhibitor in a four step reaction sequence and results in an overall yield of greater than 35%. In addition the present invention provides a method for stereoselectively preparing the (E)-isomer of the ribonucleotide reductase inhibitor.

SUMMARY OF THE INVENTION

The present invention provides a novel process for preparing a compound of the formula

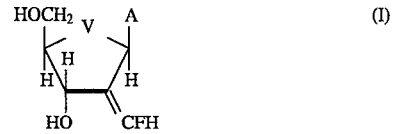

(I)

wherein

V is oxy or methylene and

A is a radical of the formula

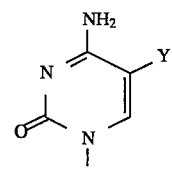

wherein Y is hydrogen, $C_1$-$C_4$ alkyl or $C_1$-$C_4$ alkoxy comprising the steps of:

(a) reacting a compound of the formula

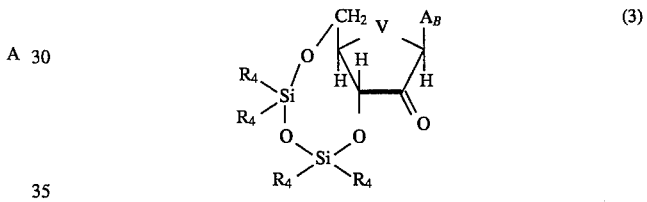

(3)

wherein $R_4$ is $C_2$-$C_7$ alkyl or $C_5$-$C_7$ cycloalkyl and $A_B$ is a radical of the formula

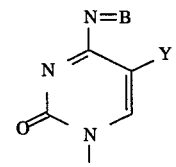

and B is a suitable nitrogen blocking group of the formula $CR_1NR_2R_3$ wherein $R_1$ is a hydrogen or $C_1$-$C_4$ alkyl and $R_2$ and $R_3$ are independently $C_1$-$C_4$ alkyl, with a suitable phosphonate ylid of the formula $(X)_2OP=CF(SO_2Ar)$ wherein Ar is an aryl group and X is a phenoxy or $C_1$-$C_4$ alkoxy to produce an exocyclic fluorovinyl sulfone;

(b) reacting the exocyclic fluorovinyl sulfone with a suitable base or suitable weak acid to produce a deprotected amine;

(c) reacting the deprotected amine with a stannylating reagent of the formula $(R)_3SnH$ wherein R is aryl or $C_1$-$C_4$ alkyl to produce an exocyclic (fluorovinyl)stannane;

(d) reacting the exocyclic (fluorovinyl)stannane with a protolysis agent and, either concomitantly or sequentially, reacting the silyl protecting group with a suitable acid or a fluoride ion source.

The present invention further provides a novel process for preparing a compound of the formula

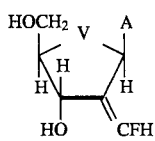  (I)

wherein
V is oxy or methylene and
A is a radical of the formula

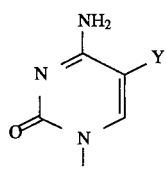

wherein Y is hydrogen, $C_1$–$C_4$ alkyl or $C_1$–$C_4$ alkoxy comprising the steps of:

(a) reacting a compound of the formula

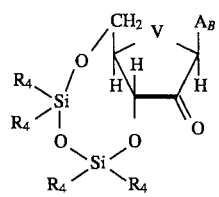  (3)

wherein $R_4$ is $C_2$–$C_7$ alkyl or $C_5$–$C_7$ cycloalkyl and $A_b$ is a radical of the formula

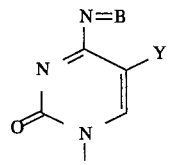

and B is a suitable nitrogen blocking group of the formula $CR_1NR_2R_3$ wherein $R_1$ is a hydrogen or $C_1$–$C_4$ alkyl and $R_2$ and $R_3$ are independently $C_1$–$C_4$ alkyl, with a suitable base or suitable weak acid to produce a deprotected amine;

(b) reacting the deprotected amine with a suitable phosphonate ylid of the formula $(X)_2OP=CF(SO_2Ar)$ wherein Ar is an aryl group and X is a phenoxy or $C_1$–$C_4$ alkoxy to produce an exocyclic fluorovinyl sulfone;

(c) reacting the exocyclic fluorovinyl sulfone with a stannylating reagent of the formula $(R)_3SnH$ wherein R is aryl or $C_1$–$C_4$ alkyl to produce an exocyclic (fluorovinyl)stannane;

(d) reacting the exocyclic (fluorovinyl)stannane with a protolysis agent and, either concomitantly or sequentially, reacting the silyl protecting group with a suitable acid or a fluoride ion source.

The present invention further provides a novel process for preparing a compound of the formula (I), comprising the steps of:

(a) reacting a compound of the formula

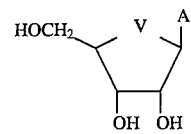  (1)

wherein A is a radical of the formula

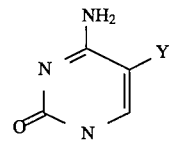

wherein Y is hydrogen, $C_1$–$C_4$ alkyl or $C_1$–$C_4$ alkoxy, with excess 1,3-dichloro-1,1,3,3-tetraalkyldisiloxane and triethylamine followed by treatment with $SO_3$-pyridine complex to produce a 3',5'-protected-2'-keto derivative;

(b) reacting the 3',5'-protected-2'-keto derivative with a suitable phosphonate ylid of the formula $(X)_2OP=CF(SO_2Ar)$ wherein Ar is an aryl group and X is a phenoxy or $C_1$–$C_4$ alkoxy to produce an exocyclic fluorovinyl sulfone;

(c) reacting the exocyclic fluorovinyl sulfone with a stannylating reagent of the formula $(R)_3SnH$ wherein R is aryl or $C_1$–$C_4$ alkyl to produce an exocyclic (fluorovinyl)stannane;

(d) reacting the exocyclic (fluorovinyl)stannane with a protolysis agent and, either concomitantly or sequentially, reacting the silyl protecting group with a suitable acid or a fluoride ion source.

The present invention further provides a process for stereoselectively preparing a compound of the formula

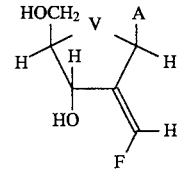  (Ia)

wherein
V is oxy or methylene; the exocyclic vinylfluoride is in the (E) configuration; and
A is a radical of the formula

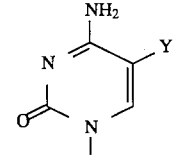

wherein Y is hydrogen, $C_1$–$C_4$ alkyl or $C_1$–$C_4$ alkoxy, comprising the steps of:

(a) reacting a compound of the formula

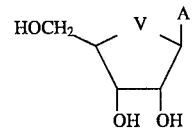  (1)

wherein A is a radical of the formula

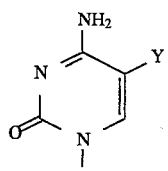

wherein Y is hydrogen, $C_1$–$C_4$ alkyl or $C_1$–$C_4$ alkoxy, with excess 1,3-dichloro-1,1,3,3-tetraalkyldisiloxane and triethylamine followed by treatment with $SO_3$-pyridine complex to produce a 3',5'-protected-2'-keto derivative;

(b) reacting the 3',5'-protected-2'-keto derivative with a suitable phosphonate ylid of the formula $(X)_2OP=CF(SO_2Ar)$ wherein the ylid is prepared from potassium tert-butoxide; Ar is an aryl group and X is a phenoxy or $C_1$–$C_4$ alkoxy to produce an exocyclic fluorovinyl sulfone in the (Z) configuration;

(c) reacting the (Z)-exocyclic fluorovinyl sulfone with a stannylating reagent of the formula $(R)_3SnH$ wherein R is aryl or $C_1$–$C_4$ alkyl to produce an exocyclic (fluorovinyl)stannane in the (Z)-configuration;

(d) reacting the (Z)-exocyclic (fluorovinyl)stannane with a protolysis agent and, either concomitantly or sequentially, reacting the silyl protecting group with a suitable acid or a fluoride ion source.

In a further embodiment the present invention provides novel compounds of the following formulas

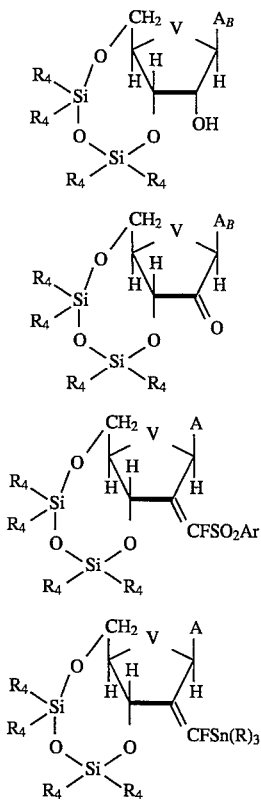

The invention further provides the novel compound (E)-2'-deoxy-2'(fluoromethylene)cytidine monohydrate of the formula;

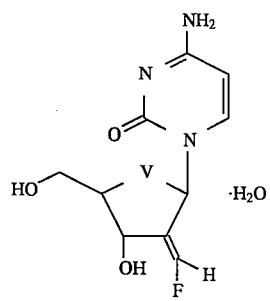

which is useful as a ribonucleotide reductase inhibitor in the treatment of patients afflicted with neoplastic or viral disease states. The above monohydrate has beneficial manufacturing characteristics over the anhydrous form of (E)-2'-deoxy-2'(fluoromethylene)cytidine.

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl and the like. The term "$C_1$–$C_4$ alkoxy" refers to an alkyloxy radical made up of an oxygen radical bearing a saturated straight or branched chain hydrocarbyl radical of one to four carbon atoms and specifically includes methoxy, ethoxy, propyloxy, isopropyloxy, n-butyloxy, isobutyloxy, sec-butyloxy, tertiary butyloxy and the like. As used herein the term "$C_2$–$C_7$ alkyl" refers to a saturated straight or branched chain hydrocarbon radical of two to seven carbon atoms. Included within the scope of this term are ethyl, n-propyl, isopropyl, n-butyl, isobutyl, sec-butyl, tert-butyl, pentyl, neopentyl, 2-methylbutyl, 3-methylbutyl, hexyl, heptyl and the like. As used herein the term "$C_5$–$C_7$ cycloalkyl" refers to a saturated cyclic hydrocarbon radical of 5 to 7 carbon atoms. Included within the scope of this term are cyclopentyl, cyclohexyl, cycloheptyl and the like. As used herein the term "1,3-dichloro-1,1,3,3-tetraalkyldisiloxane" refers to compounds wherein the alkyl substituents of the 1,3-(1,1,3,3-tetraalkyldisiloxanylidene) are defined by $R_4$. $R_4$ is a $C_2$–$C_7$ alkyl or $C_5$–$C_7$ cycloalkyl substituent. Examples of suitable $R_4$ substituents are ethyl, n-propyl, isopropyl, n-butyl, isobutyl, sec-butyl, tert-butyl, pentyl, neopentyl, 2-methylbutyl, 3-methylbutyl, hexyl, heptyl, cyclopentyl, cyclohexyl, cycloheptyl and the like. The term "halogen" or "halo" refers to a fluorine, chlorine, bromine, or iodine atom. The term "At" or "aryl" refers to an aromatic radical of from about 6 to 12 carbon atoms, such as phenyl, naphthyl or phenyl($C_1$–$C_4$)alkyl groups, wherein said groups are optionally substituted with one, two or three substituents selected from the group consisting of $C_1$–$C_4$ alkyl, halo-substituted $C_1$–$C_4$ alkyl, halogen or $C_1$–$C_4$ alkoxy. The term "phenyl($C_1$–$C_4$)alkyl" refers to a phenyl group substituted with a $C_1$–$C_4$ alkyl including phenylmethyl, phenethyl and the like. Specifically included within the scope of the term "Ar" or "aryl" are phenyl, p-toluoyl, p-methoxyphenyl, p-chlorophenyl, naphthyl and the like.

The general synthetic process of the present invention is set forth in Schemes A and AI. All the substituents, unless otherwise indicated, are previously defined. The reagents and starting materials for use in this process are readily available to one of ordinary skill in the art.

Scheme A
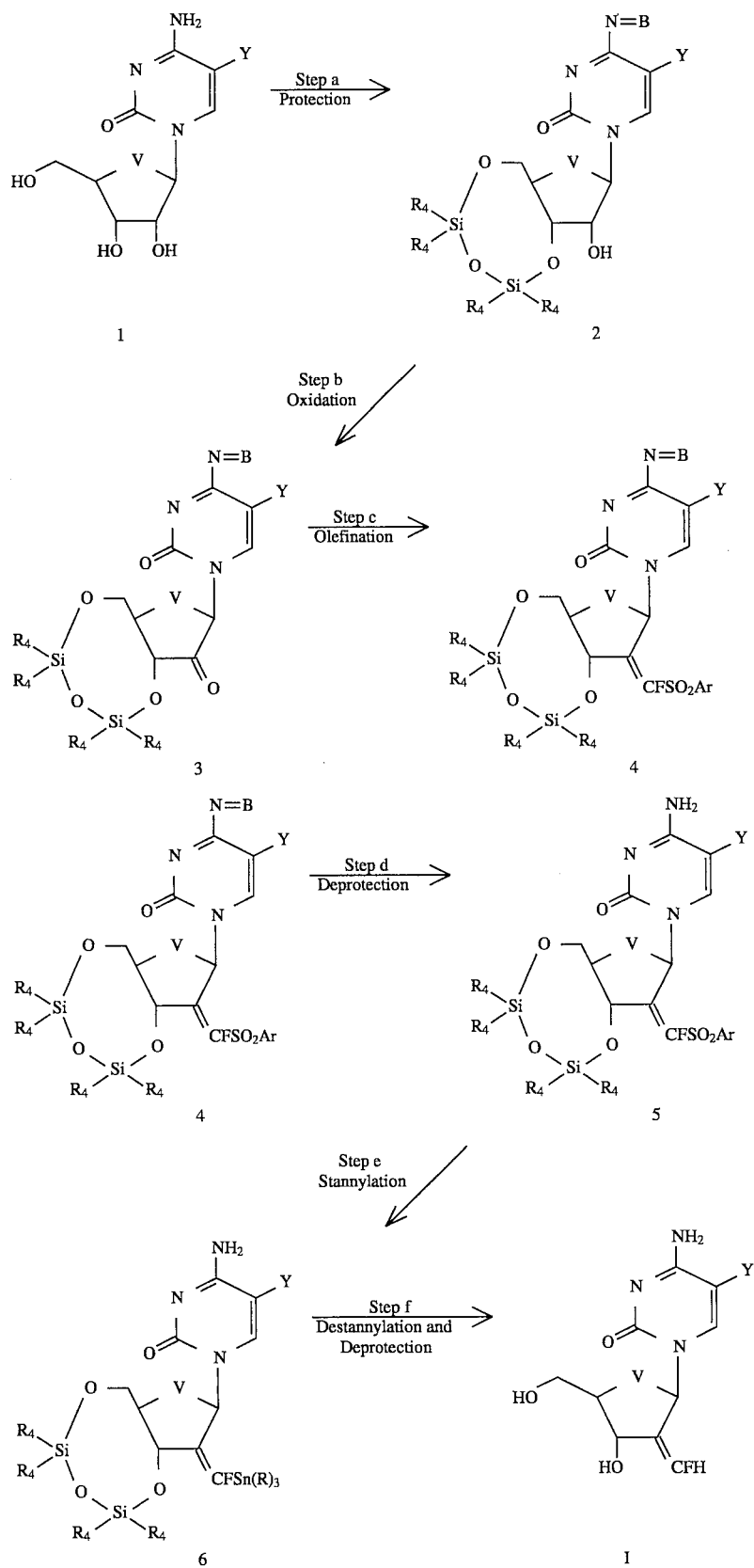

In Scheme A, step a, the 3' and 5' hydrolysis of the appropriately substituted cytidine derivative of structure (1) are protected as the 1,3-(1,1,3,3-tetraalkyldisiloxanylidene) derivative and the amino function is protected with a suitable nitrogen blocking group to provide the compound defined by structure (2). The alkyl substituents of the 1,3-(1,1,3,3-tetraalkyldisiloxanylidene) are defined by $R_4$. $R_4$ is a $C_2$–$C_7$ alkyl or $C_5$–$C_7$ cycloalkyl substituent. Examples of suitable $R_4$ substituents are ethyl, n-propyl, isopropyl, n-butyl, isobutyl, sec-butyl, tert-butyl, pentyl, neopentyl, 2-methylbutyl, 3-methylbutyl, hexyl, heptyl, cyclopentyl, cyclohexyl, cycloheptyl and the like. The preferred $R_4$ substituents are isopropyl, isobutyl, cyclopentyl and the like. The most preferred $R_4$ substituent is isopropyl. A suitable nitrogen blocking group is bound to nitrogen as the imine derivative and is stable to oxidizing conditions such as methyl sulfoxide/oxalyl chloride and to strong organic bases, such as lithium diisopropylamide. For example, suitable nitrogen blocking groups would be N-(N',N'-dimethylaminomethylene)amine, N-(methyl-N',N'-dimethylaminomethylene)amine, N-(methyl-N',N'-diethylaminomethylene)amine, N-(ethyl-N',N'-diethylaminomethylene)amine, and the like. The preferred nitrogen blocking is N-(N',N'-dimethylaminomethylene)amine.

More specifically, in Scheme A, step a, the cytidine derivative (1) is treated with an equivalent of 1,3-dichloro-1,1,3,3-tetraalkyldisiloxane in a basic organic solvent, such as pyridine and allowed to stir for 12 to 24 hours at approximately 10° C. to 30° C. The 1,3-dichloro-1,1,3,3-tetraalkyldisiloxane is readily available to one of ordinary skill in the art, for example see Zhang, H. X., et al., *Synthetic Communications*, 17(11), 1299–1307 (1987). An excess of dimethylformamide dimethyl acetal is then added to the reaction which is allowed to stir for 2 to 6 hours. The solvent is removed under vacuum and the residue purified by techniques well known to one skilled in the art to provide the compound defined by structure (2).

In Scheme A, step b, the 2'-hydroxyl group is oxidized to the ketone derivative defined by structure (3) by oxidation methods well known to one skilled in the art.

For example, approximately 1.5 equivalents of oxalyl chloride is dissolved in a suitable anhydrous organic solvent, such as methylene chloride, and cooled to about –750° C. To this solution is added 3 equivalents of methyl sulfoxide dropwise, maintaining the temperature below –55° C. An equivalent of the product defined by structure (2) is dissolved in a suitable amount of anhydrous organic solvent, such as methylene chloride, and added slowly to the reaction with stirring. After addition is complete the reaction is stirred for approximately 30 minutes at –75° C., an excess of a suitable organic base, such as triethylamine, is added and the reaction is allowed to warm to room temperature. The ketone derivative (3) is then isolated and purified by techniques well known to one skilled in the art. For example, silica gel chromatography followed by recrystallization from a suitable organic solvent or solvent mixture, such as 10% chloroform/hexane provides the ketone derivative (3).

In Scheme A, step c, the ketone derivative (3) can be olefinated to yield the corresponding exocyclic fluorovinyl sulfone (4) by reaction with a phosphorus ylide which can be prepared according to procedures which are well known and appreciated in the art of chemistry as described by March ["Advanced Organic Chemistry: Reactions, Mechanisms and Structure", McGraw-Hill Book Company, 2nd Ed., 1977, 864–872].

More specifically, olefination may be performed by reacting the appropriately substituted ketone derivative (3) with a suitable phosphonate ylide of formula $(X)_2OP=CF(SO_2Ar)$ through a modification of the Wittig reaction as described by Wadsworth et al. [*J. Am. Chem. Soc.* 1961, 83, 1733]. For example, the appropriately substituted phosphonate of formula $(X)_2OPCHF(SO_2Ar)$ is dissolved in a suitable anhydrous organic solvent and cooled to approximately –70° C. A suitable anhydrous organic solvent includes hydrocarbon solvents, dialkyl ethers, $C_1$–$C_6$ alkanes, tetrahydrofuran and the like. The preferred anhydrous organic solvent is tetrahydrofuran. An equivalent of a strong base is added slowly to produce the ylide. A wide variety of bases can be used including alkoxides and organometallics, such as alkyllithium, lithium dialkylamide, sodium hydride and the like. The preferred bases are potassium tert-butoxide and lithium bis(trimethylsilyl)amide. After approximately one hour an equivalent of the appropriately substituted ketone derivative (3) is added to the phosphonate ylide at approximately –60° C. followed by warming to about 0° C. for about 30 minutes and then warmed to room temperature for approximately 2.5 hours. The exocyclic fluorovinyl sulfone (4), is then isolated and purified by techniques well known to one skilled in the art. For example, the reaction is quenched with saturated ammonium chloride and the aqueous layer is extracted with a suitable organic solvent, such as diethyl ether. The organic phase is dried over a suitable drying agent, such as anhydrous magnesium sulfate, filtered and concentrated under vacuum. The crude material is filtered through silica gel with a suitable organic solvent, such as ethyl acetate to provide the exocyclic fluorovinyl sulfone (4).

In Scheme A, step d, deprotection of the exocyclic fluorovinyl sulfone (4) by removal of the nitrogen blocking group to provide the appropriately substituted deprotected amine derivative (5) is performed by dissolving the protected compound in an organic solvent, such as dioxane followed by treatment with an excess of a suitable base. A suitable base is one that is capable of removing the nitrogen blocking group without removing the silyl protecting group at the 3',5' positions. Examples of suitable bases are ammonium hydroxide, ammonia, methylamine and the like. The preferred suitable base is ammonium hydroxide. The reaction is stirred for about 8 to 24 hours at room temperature and the deprotected amine (5) is isolated and purified by techniques well known to one skilled in the art. For example, the solvent is removed under vacuum azeotroping off the water with addition of ethanol and the crude material is purified by flash chromatography using a suitable solvent mixture, such as 5% hexane/ethyl acetate to provide the deprotected amine (5).

An alternative procedure for preparation of the deprotected amine (5) is performed by dissolving the appropriately substituted exocyclic fluorovinyl sulfone (4) in an organic solvent, such as ethyl acetate and treating with one equivalent of concentrated ammonium hydroxide for approximately 2 hours at room temperature. The deprotected amine (5) is isolated and purified by techniques well known to one skilled in the art. For example, the solvent is removed under vacuum azeotroping off the water with addition of ethanol and the crude material is purified by flash chromatography using a suitable solvent mixture, such as 5% hexane/ethyl acetate to provide the deprotected amine (5).

In Scheme A, step e, stannylation of the deprotected amine (5) utilizing procedures which are known to one of ordinary skill in the art as described by McCarthy et al. *J. Am. Chem. Soc.*, 1991, 113, 7439] provides the exocyclic (fluorovinyl)stannane of structure (6). For example, the deprotected amine (5) is dissolved in a suitable organic solvent, such as benzene or cyclohexane and treated with an excess of a suitable stannylating reagent of formula $(R)_3SnH$. Suitable stannylating reagents are tributyltin hydride, triethyltin hydride, trimethyltin hydride, triphenyltin hydride and the like. The preferred stannylating reagent is tributyltin hydride. The reaction is then initiated by employing a suitable initiator. Suitable initiators are azobisisobutyronitrile (AIBN), UV light, heat and the like. The preferred suitable initiator is azobisisobutyronitrile (AIBN). A catalytic amount of AIBN is added and the reaction is heated at about 60° to 80° C. for about 18 to 20 hours. Additional AIBN may be added as required to convert all the starting material to product. The additional AIBN can be added portionwise directly or as a solution in tetrahydrofuran during the course of the reaction. The additional amount of AIBN required can be readily determined by one of ordinary skill in the art by following the disappearance of starting material in the reaction utilizing techniques well known in the art, such as HPLC or thin layer chromatography. The product is then isolated and purified by techniques well known to one skilled in the art to provide the exocyclic (fluorovinyl)stannane defined by structure (6). For example, the reaction is concentrated under vacuum and the residue is purified by flash chromatography using a suitable solvent mixture, such as 4% to 6% methanol/methylene chloride to provide exocyclic (fluorovinyl)stannane (6).

In Scheme A, step f, the exocyclic (fluorovinyl)stannane (6) can be sequentially converted to the exocyclic fluorovinyl derivative of Formula I by first destannylating with a protolysis agent under mild conditions in the absence of a fluoride ion source. A suitable protolysis agent will substitute a proton for the stannane substituent. Examples of a protolysis agent are ammonia/methanol, silica gel and the like. The protected exocyclic vinylfluoride is then deprotected by treatment with a suitable acid, such as aqueous hydrochloric acid or a fluoride ion source to provide the exocyclic vinylfluoride of Formula I. Examples of a fluoride ion source are sodium fluoride, potassium fluoride, cesium fluoride, tetrabutylammonium fluoride, ammonium fluoride and the like. The preferred fluoride ion source is potassium fluoride.

For example, in Scheme A, step f, the exocyclic (fluorovinyl)stannane (6) is combined with excess silica gel as described by Stork et al. [*J. Am. Chem. Soc.* 1987, 109, 829] in a suitable organic solvent, such as methanol and allowed to stir until removal of the tributyltin is complete. The protected exocyclic vinylfluoride is then isolated and purified by techniques well known to one skilled in the art, such as flash chromatography. This product is then treated with an excess of a fluoride ion source, such as tetrabutylammonium fluoride, in a suitable organic solvent, such as methanol and allowed to stir until the deprotection is complete. The product is then isolated and purified by techniques well known to one of ordinary skill in the art to provide the exocyclic fluorovinyl compound defined by Formula I. For example, the reaction is concentrated under vacuum and purified by flash chromatography using a suitable solvent mixture, such as 50% ethyl acetate/hexane followed by 10% to 20% methanol/ethyl acetate. Recrystallization from methanol/ethyl acetate provides the compound of Formula I.

In Scheme A, step f, the exocyclic (fluorovinyl)stannane (6) can also be destannylated and deprotected concomitantly by reacting it with a protolysis agent and fluoride ion source or a suitable acid to provide the exocyclic vinylfluoride of Formula I.

For example, in Scheme A, step f, the exocyclic (fluorovinyl)stannane (6) is dissolved in a suitable organic solvent, such as methanol, treated with a protolysis agent such as potassium fluoride(KF may be in the dihydrate form), which also acts as a fluoride ion source and the reaction is heated at about 45° to 65° C. for approximately 24 to 48 hours. After cooling, the solvent is partially concentrated and excess silica gel is added. The remaining solvent is removed and the product is isolated and purified by techniques well known to one of ordinary skill in the art to provide the compound defined by Formula I. For example, the reaction is concentrated under vacuum and purified by flash chromatography using a suitable solvent mixture, such as 50% ethyl acetate/hexane followed by 10% to 20% methanol/ethyl acetate. Recrystallization from methanol/ethyl acetate provides the compound of Formula I.

Of course one skilled in the art would understand that the stepwise synthesis as presented in Scheme A is not limited to the particular sequence of steps as presented.

For example, in Scheme A, step c the olefination reaction may be performed subsequent to the deprotection reaction performed in step d.

An additional general synthetic process for preparation of compounds of formulas I and Ia is set forth in Scheme AI. All the substituents, unless otherwise indicated, are previously defined. The reagents and starting materials for use in this process are readily available to one of ordinary skill in the art.

Scheme AI

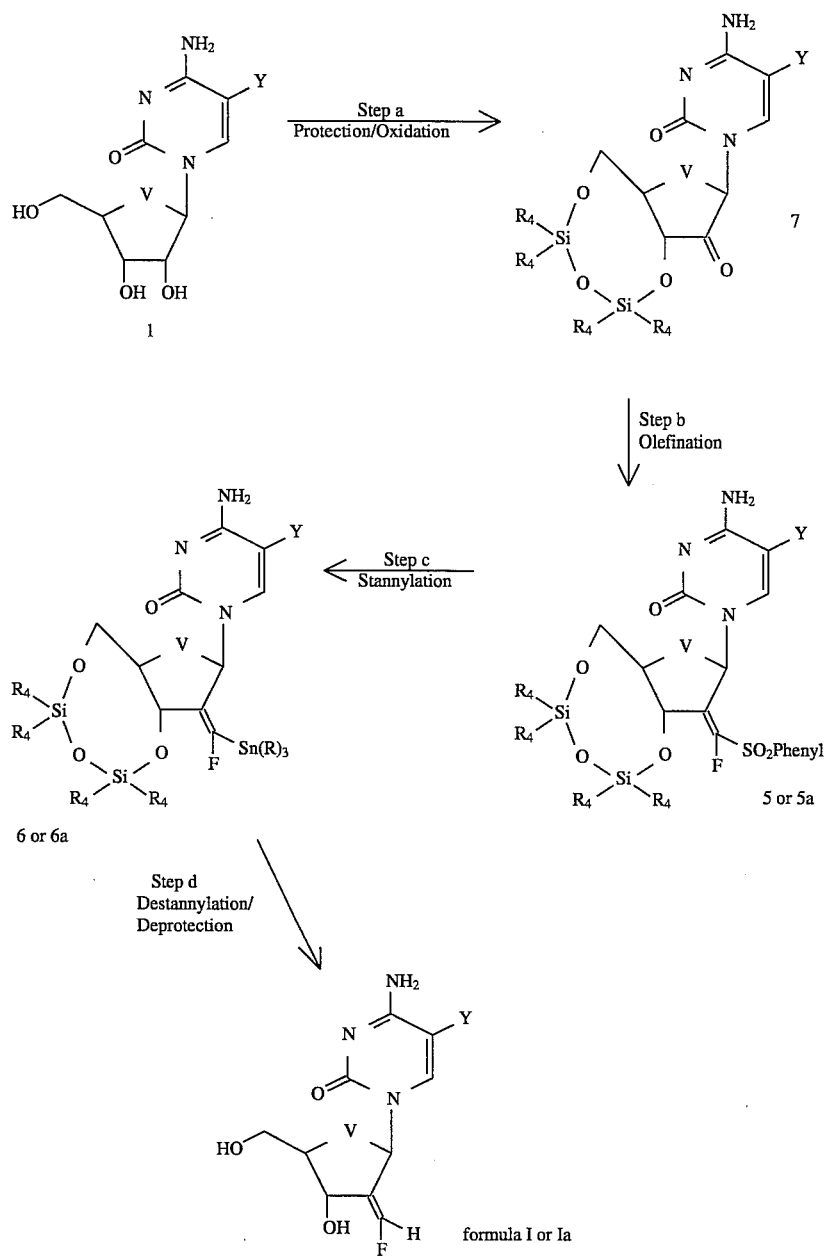

In Scheme AI step a, the 3' and 5' hydrolysis of the cytidine derivative of structure (1) are protected as the 1,3-(1,1,3,3-tetraalkyldisiloxanylidene) derivative and the 2' hydroxyl is oxidized to the ketone derivative as described by structure (7). For example, cytidine is combined with an excess of 1,3-dichloro-1,1,3,3-tetraalkyldisiloxane in a suitable dry organic solvent, such as pyridine under an inert atmosphere, such as nitrogen. The slurry is stirred at room temperature for about 5 to 24 hours and then cooled to about −17° to 5° C. Approximately 7 equivalents of dry triethylamine are added over a time period of about 1 hour followed by approximately 10 to 11 equivalents of dry dimethyl sulfoxide. Approximately 3 equivalents of $SO_3$-pyridine complex are added and the mixture is stirred at about −5° to 5° C. for about 10 to 20 hours. The reaction is then poured into a mixture of ethyl acetate/water (2:1 by weight) which has been cooled to about 5° C. The original reactor is rinsed with a mixture of ethyl acetate/water (1.2:1.0 by weight) which is added to the previously quenched reaction mixture. Approximately 0.8 equivalents of "OXONE" (potassium peroxymonosulfate) are added to the mixture to oxidize dimethyl sulfide side-product, while maintaining the internal temperature of the reaction mixture below 15° C. The reaction is stirred for about 0.2 hours and then it is filtered to remove salts. The filter cake is rinsed with a suitable organic solvent, such as ethyl acetate. The product is then isolated by techniques well known in the art. For example, the liltrate phases are then separated and the organic phase is rinsed with water. The organic phase is substantially concentrated under vacuum and toluene is added. Again the mixture is substantially concentrated under vacuum. The toluene addition concentration procedure is continued until the distillate is water free. Toluene is again added, the mixture is cooled to about 15° C. and then it is filtered. The filter cake is rinsed with toluene and dried at about 35° C. under a flow of nitrogen to provide the 3',5'-protected-2'-keto derivative (7) as a white solid.

In Scheme AI step b, the 3',5'-protected-2'-keto derivative (7) is subjected to an olefination reaction to provide the (Z)-exocyclic fluorovinyl sulfone described by structure (5) following the procedure described previously in Scheme A step c. More specifically, the olefination reaction can be performed to stereoselectively produce the (Z)-isomer of the exocyclic fluorovinyl sulfone (5a). For example, approximately 1.05 equivalents of diethyl-1-fluoro-1-phenylsulfonylmethanephosphonate and a dry organic solvent, such as tetrahydrofuran are combined under an inert atmosphere such as nitrogen. The mixture is cooled to about –40° C. and an equivalent of ketone derivative (7) is added to the slurry with stirring. The mixture is then cooled to about –50° C. and approximately 1.03 equivalents of a potassium t-butoxide solution (about 20% in tetrahydrofuran) is added dropwise over a period of about 3 hours. After the addition is complete the reaction is allowed to warm to approximately –15° C. over about 3 hours. Additional tetrahydrofuran may be added to aid in stirring as the reaction may thicken. The product is then isolated by techniques well known in the art. For example, the reaction can be quenched by vacuum transferring to an aqueous ammonium chloride solution at room temperature. The mixture is allowed to stir for about 30 minutes. The phases are then allowed to separate. The organic phase containing the (Z)-exocyclic fluorovinyl sulfone (5a) is separated from the aqueous phase and is carried on to step c in Scheme AI.

In Scheme AI step c, the exocyclic fluorovinyl sulfone (5) or the (Z)-exocyclic fluorovinyl sulfone (5a) is subjected to a stannylation reaction to provide the exocyclic (fluorovinyl)stannane or the (Z)-exocyclic (fluorovinyl)stannane described by structures (6) and (6a) under conditions generally described previously in Scheme A step e.

In Scheme AI step d, the exocyclic (fluorovinyl)stannane (6) or the (Z)-exocyclic (fluorovinyl)stannane (6a) can be sequentially or concomitantly destannylated and deprotected to provide the the exocyclic vinylfluoride of Formula I or the (E)-exocyclic vinylfluoride of Formula Ia under conditions generally described previously in Scheme A step f.

The appropriately substituted phosphonate of formula $(X)_2OPCHF(SO_2Ar)$ required for preparation of the phosphonate ylide for reaction in Scheme A in step c and Scheme AI in step b can be obtained by a variety of methods described by Schemes B, C and D.

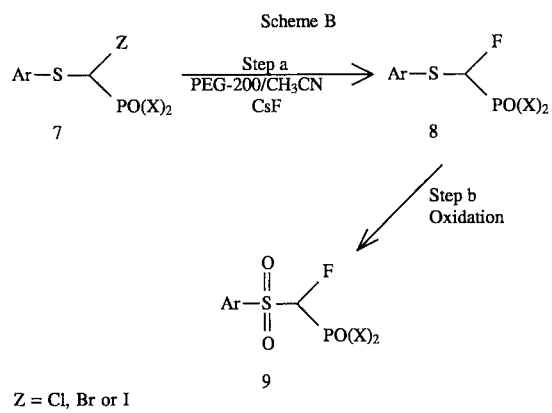

Z = Cl, Br or I

For example in Scheme B, step a, the compound defined by structure (7) is dissolved in a mixture of poly(ethylene glycol):acetonitrile in a ratio of approximately 1:2. A suitable molecular weight range for the poly(ethylene glycol) is between 100 and 400 g/mol. An excess of a fluoride ion source, such as cesium fluoride is added and the reaction is heated to approximately 80° C. for 1 to 24 hours. The reaction is then diluted with water and the product extracted with a suitable organic solvent such as chloroform to provide after drying and concentrating under vacuum the product defined by structure (8). This is then oxidized by techniques well known to one skilled in the art. For example, treatment of compound (8) with potassium peroxymonosulfate in a suitable organic solvent, such as aqueous methanol to provides the appropriately substituted phosphonate defined by structure (9).

Phe appropriately substituted phosphonate defined by structure (9) can be obtained by another method as described in Scheme C.

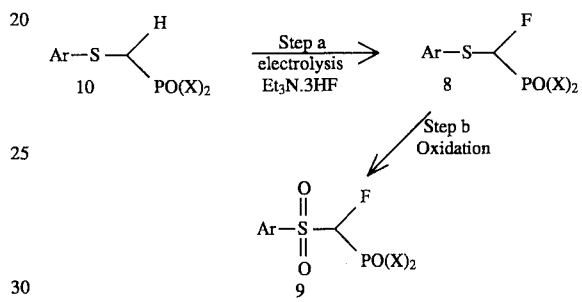

In Scheme C, step a, the compound defined by structure (10) is dissolved in a suitable organic solvent, such as tetrahydrofuran, treated with excess triethylamine trihydrofluoride and the solution is cooled to approximately –78° C. The solution is then subjected to a controlled potential electrolysis for about 3 to 10 hours to effectuate anodic monofluorination following generally the procedure of Matsue et al. [*J. Chem. Soc. Chem. Commun.* 1991, 1028]. The product defined by structure (8) is then isolated and oxidized in step b as described in Scheme B to provide the appropriately substituted phosphonate defined by structure (9).

Additionally, the appropriately substituted phosphonate defined by structure (9) may be prepared in situ as the ylide defined by the formula $(X)_2OP=CF(SO_2Ar)$ as shown in Scheme D.

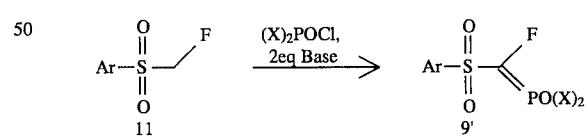

In Scheme D, the appropriately substituted sulfone, such as fluoromethylphenyl sulfone, which can be prepared according to McCarthy et al. [*Tetrahedron Lett.* 1990, 31, 5449], is dissolved in a suitable anhydrous organic solvent, such as tetrahydrofuran, cooled to approximately –70° C. and treated with an equivalent of a dialkyl chlorophosphate, such as diethyl chlorophosphate, defined by the formula $(X)_2POCl$. The solution is then treated slowly with 2 equivalents of a strong base, such as lithium bis(trimethylsilyl)amide. After addition is complete the reaction is stirred at approximately –65° C. for about 1 hour to provide the ylide defined by structure (9').

The following examples present typical syntheses as described by Schemes A, B, C and D. These examples are understood to be illustrative only and are not intended to limit the scope of the invention in any way. As used in the following examples, the following terms have the meanings indicated: "g" refers to grams, "mmol" refers to millimoles, "mL" refers to milliliters, "°C." refers to degrees Celsius, "TLC" refers to thin layer chromatography, "mg" refers to milligrams, "μL" refers to microliters and "δ" refers to parts per million downfield from tetramethlysilane.

EXAMPLE 1

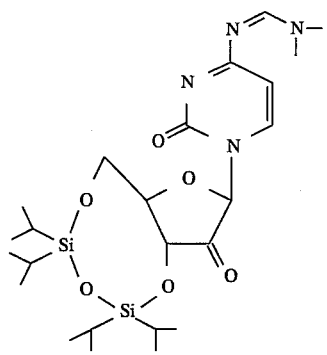

2'-deoxy-N-[(dimethylamino)amino)methylene]-2'-oxo-3',5'-O-[1,1,3,3-tetrakis(1-methylethyl)-1,3-disiloxanediyl]-citidine Scheme A, step a; In a one-neck 2 L round bottom flask equipped with an addition funnel and under a nitrogen atmosphere, treat a slurry of cytidine (100 g, 0.41 mol) in anhydrous pyridine (800 mL) with 1,3-dichloro-1,1,3,3-tetraisopropyldisiloxane (130 g, 0.41 mol). After 30 minutes, everything dissolves. Stir the reaction overnight at room temperature. Add neat dimethylformamide dimethyl acetal (165 g, 1.38 mol) and stir the reaction for 4 hours. The reaction will warm slightly and become cloudy. Remove the pyridine under high vacuum and azeotrope with toluene (2×500 mL) to remove any remaining pyridine. Heat the solid residue with 1 L of ethyl acetate and gravity filter into a 5 L flask. Dissolve the insolubles in water (800mL) and brine (200mL) and extract additional product into ethyl acetate (2×600 mL). Dry the solution over anhydrous magnesium sulfate and concentrate under vacuum to provide 90 g of "wet" solid. Dissolve this solid in ethyl acetate (200 mL) and combine with the previous ethyl acetate flitrate. Add hexane (3 L) to the solution, heat and filter while still hot. Allow the solution to sit overnight. Collect the white crystals which form by filtration and dry in a warm vacuum oven to produce compound (142.4 g, 64%). Concentrate the above liltrate and purify the residue by flash chromatography on 1.4 L silica gel (12.5% ethanol/ethyl acetate) to yield an additional amount of compound (17.4 g) from fractions 8–16. Fractions 2–7 contain compound contaminated with pyridine. Concentrate these fractions under vacuum and recrystallize the residue to provide an additional amount of compound (24.5 g) to provide a total amount of 184.2 g (83% yield) of N-[(dimethylamino)methylene]-3',5'-O-[1,1,3,3-tetrakis(1-methylethyl)-1,3-disiloxanediyl]-cytidine as white crystals, mp 137°–138° C.;

$^1$H NMR (CDCl$_3$) δ0.97–1.10 (m, 28), 3.14 (s, 3), 3.16 (s, 3), 3.98–4.39 (m, 5), 5.82 (s, 1), 6.05 (d, 1, J=7.2 Hz), 7.92 (d, 1, J=7.5 Hz), 8.85 (s, 1); MS (CI/CH$_4$) m/z 541 (MH$^+$).

Anal. Calcd for C$_{24}$H$_{44}$N$_4$O$_6$Si$_2$: C, 53.30; H, 8.20; N, 10.36. Found: C, 52.93; H, 8.33; N, 10.07.

Scheme A, step b; Flush a 3 neck 2 L flask fitted with a condenser, mechanical stirrer and a thermometer with nitrogen and charge with oxalyl chloride (13.08 mL, 0.15 mol) and anhydrous methylene chloride (750 mL). Cool the solution to −75° C. and add dimethylsulfoxide (21.3 mL, 0.30 mol) dropwise while maintaining the temperature below −55° C. Continue stirring for 5 minutes and then add the protected cytidine formed above in step a (54 g, 0.10 mol) in anhydrous methylene chloride (250 mL) over 10 minutes. Stir for 30 minutes at −75° C. and add triethylamine (75.5 mL, 0.54 mol). Remove the ice bath allowing the reaction to warm to room temperature. After 1 hour at room temperature, dilute the reaction with an equal volume of diethyl ether and stir for an additional hour. Pour the mixture onto silica gel (500 mL) in a fritted funnel and elute with diethyl ether (1 L) followed by methylene chloride (1 L). Concentrate the diethyl ether wash and treat with 10% chloroform/hexane (300 mL). Filter the solid and dry to provide 31.6 g as a white powder. Concentrate the methylene chloride wash and recrystallize the residue from 10% chloroform/hexane (300 mL) to provide an additional 12.5 g for a total of 48.6 g of the title compound (90% yield). This compound readily hydrates at the C-2' position to form the ketone hydrate. It should be protected from prolonged exposure to moisture;

$^1$H NMR (CDCl$_3$) δ0.99–1.16 (m, 28), 3.13 (s, 3), 3.14 (s, 3), 3.95–4.03 (m, 1), 4.06–4.22 (m, 2), 4.93 (s, 1), 5.22 (d, 1, J=8.0 Hz), 6.02 (d, 1, J=7.2 Hz), 7.29 (d, 1, J=7.2 Hz), 8.82 (s, 1); MS (CI/CH$_4$) m/z 539 (MH$^+$).

Anal. Calcd for C$_{24}$H$_{42}$N$_4$O$_6$Si$_2$.1/15 CHCl$_3$: C, 52.85; H, 7.75; N, 10.24. Found: C, 52.72; H, 7.86; N, 10.24.

EXAMPLE 2

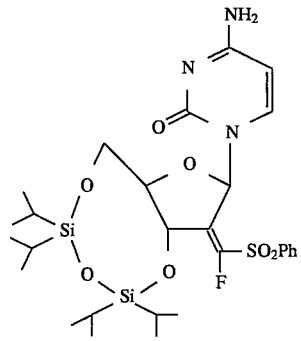

(2'Z)-2'-deoxy-2'-[fluoro(phenylsulfonyl)methylene]-3',5'-O-[1,1,3,3-tetrakis(1-methylethyl)-1,3-disiloxanediyl]-cytidine Scheme A, steps c and d; Under a nitrogen atmosphere, cool fluoromethylphenyl sulfone (19.4 g, 0.11 mol) in anhydrous tetrahydrofuran (800 mL) to −70° C. and add diethyl chlorophosphate (16 mL, 0.11 mol) via syringe. Next, slowly add 1M lithium bis(trimethylsilyl)amide (200 mL, 0.20 mol) using a dropping funnel. After complete addition maintain the reaction at −65° C. for 1 hour. Add a solution of the above prepared ketone (40 g, 0.074 mol in 200 mL of tetrahydrofuran) using an addition funnel and maintain the temperature at −60° C. After complete addition, warm to 0° C. for 30 minutes and then room temperature for 2.5 hours. Quench the reaction with saturated ammonium chloride (100 mL), dilute with diethyl ether (600 mL) and a small amount of water to dissolve the inorganic salts. Separate the layers and wash the organic phase with saturated sodium chloride. Combine the aqueous washes and back extract with diethyl ether (200 mL). Wash this organic phase with saturated sodium chloride. Combine the organic layers, dry over anhydrous magnesium sulfate, filter and concentrate under vacuum to provide a dark viscous oil (71.8 g). $^{19\,F}$ NMR (CDCl$_3$) shows four peaks, two from protected amino δ–115.21 (Z isomer) and –119.70 (E isomer) and two peaks from the free amino derivative δ–115.62 (Z isomer) and –119.40 (E isomer). The E/Z ratio is 10.4:1. Filter the crude sample through silica gel (1 L) with ethyl acetate (12 L). This step is optional before removing the amino protecting group. Concentrate the filtrate under vacuum to provide a viscous tan oil (46.8 g). Dissolve the oil in dioxane (200 mL) and add concentrated ammonium hydroxide (100 mL). Stir the reaction overnight. Then remove the solvent under vacuum and azeotrope the residue with ethanol (2×300 mL) to remove any residual water. Purify the product by flash chromatography (1.4 L silica gel, 5% hexane/ethyl acetate) to provide the E isomer (20 g). Purify isolated impure material (16 g) from flash chromatography by Prep HPLC (ethyl acetate) to provide additional E isomer (11.4 q) for a total of 31.4 g (66.3% yield) of the title compound. Recrystallize from hexane to provide a white powder, mp waxes at 135° C., clears at 145° C.;

$^1$ H NMR (CDCl$_3$) δ0.97–1.11 (m, 28), 3.93–4.03 (m, 2), 4.09–4.17 (m, 1), 5.68 (d, 1, J=7.2 Hz), 5.72 (br s, 2), 6.43 (t, 1, J=2.0 Hz), 7.33 (d, 1, J=7.5 Hz), 7.46–7.65 (m, 5); $^{19}$F NMR (CDCl$_3$) δ–119.22 (s); MS (CI/CH$_4$) m/z 640 (MH$^+$).

Anal. Calcd for C$_{28}$H$_{42}$FN$_3$O$_7$SSi$_2$: C, 52.56; H, 6.61; N, 6.57. Found: C, 52.40; H, 6.96; N, 6.36.

EXAMPLE 3

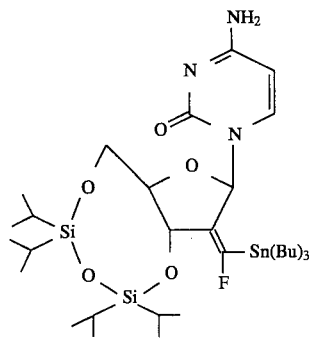

(2'Z)-2'-deoxy-2'-[fluoro(tributylstannyl)methylene]-3',5'-O-]1,1,3,3-tetrakis(1-methylethyl)-1,3-disiloxanediyl]-cytidine Scheme A, step e; Dissolve the above prepared fluorovinyl sulfone (26 g, 0.0406 mol) in benzene (300 mL) and reflux without a condenser for 15 minutes. Cool the reaction and add tributyltin hydride (32.6 mL, 0.122 mol) and azobisisobutyronitrile (500 mg). Reflux the reaction for 18 hours. Concentrate the reaction under vacuum and purify the residue by flash chromatography (1.4 L silica gel, 4% methanol/methylene chloride, 4 L, followed by 6% methanol/methylene chloride ) to provide the title compound (26.5 g, 82.8% yield) as a yellow foam; $^1$H NMR (CDCl$_3$) δ 0.87 (t, 9), 0.94–1.17 (m, 34), 1.22–1.35 (m, 6), 1.38–1.50 (m, 6), 3.78–3.88 (m, 2), 3.96–4.04 (m, 1), 5.18 (br s, 1), 5.82 (d, 1, J=7.5 Hz), 6.76 (br s, 1), 7.21 (d, 1, J=7.7 Hz); $^{19}$F NMR (CDCl$_3$) δ–92.27 (s, 84%) and (d, 16%, J$_{Sn-F}$=219 Hz); MS (CI/CH$_4$) m/z 790 (MH$^+$).

EXAMPLE 4

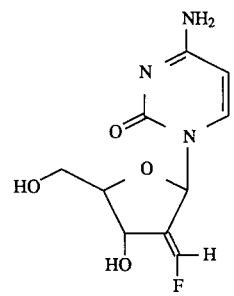

(E)-2'-deoxy-2'(fluoromethylene)cytidine

Scheme A, step f; Dissolve the (fluorovinyl)stannane (26 g, 0.033 mol) formed above and potassium fluoride (9.6 g, 0.165 mol) in methanol (300 mL) and reflux for 24 hours. After cooling, partially concentrate the solution was under vacuum, add silica gel (75 mL) and then concentrate the mixture under vacuum to a free flowing powdery solid. Purify by filtering through silica gel (1 L) with 50% ethyl acetate/hexane (2 L), followed by 10% methanol/ethyl acetate (2 L) and 20% methanol/ethyl acetate (8 L) to provide 9.3 g of compound as a white solid [note- a lower R$_f$ material visible by potassium permanganate stain, elutes with the later fractions. Trituration with diethyl ether lowers the concentration but traces still remain. Partition the product between water and diethyl ether and then lyophilize the aqueous layer to purify]. Recrystallize from methanol/ethyl acetate (120 mL) to yield 4.16 g and a second crop to yield 1.66 g of the title compound (6.26 g total, 68.7%) as white crystals, mp 166° C. (foams); $^1$H NMR (DMSO-d$_6$) δ3.48–3.62 (m, 2), 3.73–3.78 (m, 1), 4.73–4.78 (m, 1), 4 95 (t, 1, J=5.6 Hz), 5.65 (d, 1, J=6.9 Hz), 5.73 (d, 1, J=7.6 Hz), 6.65–6.68 (m, 1), 6.77 (dt, 1, J=8.13, 2.0 Hz), 7.25 (br s, 1), 7.54 (d, 1, J=7.3 Hz); $^{19}$F NMR (DMSO-d$_6$) δ–130.05 (d, J=80.9 Hz); MS NEG (CI/CH$_4$) 257 (M$^-$.).

Anal. Calcd for C$_{10}$H$_{12}$FN$_3$O$_4$: C, 46.70; H, 4.70; N, 16.34. Found: C, 46.81; H, 4.71; N, 16.18.

EXAMPLE 5

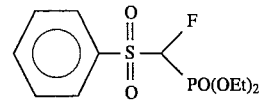

Diethyl 1-fluoro-1-(phenylsulfonyl)methanephosphonate

Scheme B, step a; Charge a 3 neck 100 mL round bottom flask flushed with nitrogen with diethyl 1-chloro-1-(phenylsulfide)methanephosphonate (62 mmol), cesium fluoride (126 mmol) and a mixture of poly(ethylene glycol)-200 and acetonitrile (38 mL of in a 1:2 ratio). Heat the reaction to 80° C. with stirring for 2 hours. Cool the reaction, dilute with water (125 mL) and extract with chloroform (2×125 mL). Combine the organic extracts, wash with water (50 mL), dry over anhydrous magnesium sulfate, filter and concentrate under vacuum to yield diethyl 1-fluoro-1-(phenylsulfide)methanephosphonate.

Scheme B, step b; Dissolve the crude diethyl 1-fluoro-1-(phenylsulfide)methanephosphonate in methanol (85 mL) and cool to 0° C. Add a solution of potassium peroxymonosulfate (63 mmol in 85 mL water) slowly with stirring. The temperature increases to approximately 55° C. After cooling, stir the reaction for 4 hours and then concentrate the reaction under vacuum. Suction filter the remaining slurry through diatomaceous earth and rinse with chloroform. Separate the layers and extract the aqueous with chloroform. Combine the organic extracts, dry over anhydrous magnesium sulfate, filter and concentrate under vacuum. The residue is then purified by techniques well known to one skilled in the art, such as flash chromatography to provide the title compound.

EXAMPLE 6

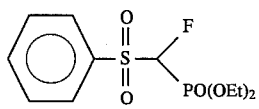

Diethyl 1-fluoro-1-(phenylsulfonyl)methanephosphonate

Scheme C, step a; Cool a solution of diethyl 1-(phenylsulfide)methanephosphonate (20 g, 76.8mmol) and triethylamine trihydrofluoride (37 g, 230 mmol) in tetrahydrofuran (200 mL) to −78° C. Electrolysis is performed at platinum electrodes (3.8×12 cm) for 15 minutes at 0.5 A and then increased to 1.0 A for 6.25 hours and then stopped. After sitting overnight, continue the electrolysis for an additional 3 hours at 1.0 A for a total time of 9.5 hours. Dilute the reaction with diethyl ether (200 mL) and rinse with 2 molar ammonium hydroxide. Wash the aqueous and extract with diethyl ether (200 mL). Combine the organic phases and dry over anhydrous magnesium sulfate. Filter and concentrate to provide the crude material as a brown oil (27.4 g). Purify the crude material by passing through silica gel (500 g, 60–200 mesh) with ethyl acetate:hexane (1:6, 4 L then 1:3, 2 L) followed by ethyl acetate to provide the diethyl 1-fluoro-1-(phenylsulfide)methanephosphonate (10.7 g, 50%). Scheme C, step b; Oxidize the diethyl 1-fluoro-1-(phenylsulfide)methanephosphonate (8.4 g, 86% pure) in a manner analogous to that in example 5, step b by dissolving in methanol (200 mL) and treating with potassium peroxymonosulfate (35g in 300 mL water) to provide the title compound.

EXAMPLE 7

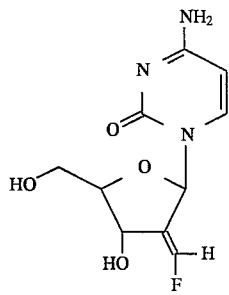

(E)-2'-deoxy-2'(fluoromethylene)cytidine

Scheme A, step f [sequential method]; Dissolve (Z)-2'-deoxy-2'-[fluoro(tributylstannyl)methylene]-3',5'-O-[1,1,3,3-tetrakis(1-methylethyl)-1,3-disiloxanediyl]-cytidine (8 g, 0.01 mol) prepared in example 3 in methylene chloride (200 mL), add activated silica gel (approximately 50 g, 60–200 mesh) and stir until TLC indicates the protolysis is complete. Filter the reaction and concentrate the filtrate under vacuum to yield the protected exocyclic vinylfluoride. Dissolve the protected exocyclic vinylfluoride (0.01 mol) in tetrahydrofuran (200 mL) and treat with tetrabutylammonium fluoride (0.025 mol). Stir the reaction until TLC indicates removal of the 3',5' protecting group is complete. The product is then isolated and purified by techniques well known to one of ordinary skill in the art to provide the title compound.

EXAMPLE 8

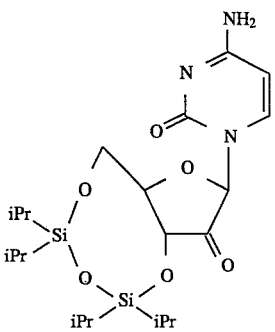

Preparation of 2'-Deoxy-2'-oxo-3',5'-O-[1,1,3,3-tetrakis(1-methylethyl)-1,3-disiloxanediyl]-cytidine Cytidine (7 Kg, 28.8 mmol), dry pyridine (29.6 Kg, 374.7 mol) and 1,3-dichloro-1,1,3,3-tetraisopropyldisiloxane (10.0 Kg, 31.7 mol) are loaded into a nitrogen-purged 50 gallon glass lined reactor. The slurry is stirred at room temperature for 6 hours then cooled to −17° C. Dry triethylamine (20.7 Kg, 204.8 mol ) is added over one hour. During the addition the reaction temperature rises to −2° C. Dry dimethyl sulfoxide (30.3 Kg, 387.5 mol) and SO₃-pyridine complex (14.0 Kg, 87.7 mol) are added in one portion and the mixture is stirred between −5° and 5° C. After 10 hours the mixture is quenched by transferring to a 100 gallon glass-lined reactor containing ethyl acetate (77.3 Kg ) and water (32.2 Kg ) cooled to 5° C. The original reactor is rinsed with a mixture of ethyl acetate (18.4 Kg) and water (15.1 Kg) and this is transferred to the quench reactor. A 20 wt % solution of OXONE (70.9 Kg, 23.1 mol) is added to the two phase mixture keeping the internal temperature below 15° C. Stir the mixture for 0.2 hours and then filter to remove salts, rinsing the cake with ethyl acetate (26.4 Kg). Allow the filtrate phases to separate. The bottom aqueous phase is drained and the top organic phase is washed with water (28.4 Kg). The organic phase is then concentrated under vacuum (70 mmHg, 20° C.) to a volume of about 20 gallons. Toluene (173 Kg) is added and the mixture is concentrated under vacuum (60 mm HG, 30° C.) to about 50 gallons. The toluene addition/concentration is continued until the overheads become clear (water free). The mixture is then concentrated under vacuum to about 35 gallons. The mixture is cooled to 15° C. and filtered. The filter cake is rinsed with toluene (177 Kg). The filter cake is then dried at 35° C. under a flow of nitrogen provided the title compound (8.6 Kg, 62%) as a white solid.

EXAMPLE 9

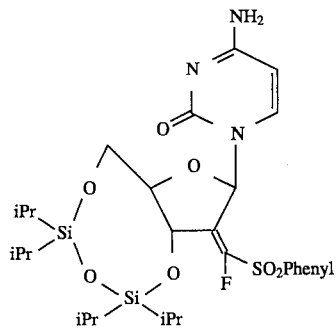

Preparation of
(Z)-2'-[fluoro(phenylsulfonyl)methylene]-3',5'-O-
[1,1,3,3-tetrakis(1-methylethyl)-1,3-disiloxanediyl]-
cytidine Diethyl-1-fluoro-1-phenylsulfonylmethanephosphonate (1.391 Kg, 4.483 mol) and dry tetrahydrofuran (8.328 Kg) are combined in a nitrogen-purged five-neck 22 liter round bottom flask equipped with a 6 liter addition funnel, a mechanical stirrer, a nitrogen bubbler and a thermowell. The resulting solution is cooled to −40° C. Ground 2'-deoxy-2'-oxo-3',5'-O-[1,1,3,3-tetrakis (1-methylethyl)-1,3-disiloxanediyl]cytidine (2.064, 4.266 mol) is then aclaea in one portion and the resulting slurry cooled to −50° C. Potassium t-butoxide (20wt % in tetrahydrofuran, 2.461 Kg, 4.387 mol) is then added dropwise via the addition funnel over 3 hours. After addition is complete, the homogeneous brown mixture is slowly warmed to −15° C. over 3 hours. The mixture thickens during warm-up. Additional tetrahydrofuran (1.294 Kg) is added to improve stirring. The reaction mixture is then quenched by vacuum transferring to a room temperature solution of ammonium chloride (1.706 Kg) in water (5.242 Kg) and this is stirred for 0.5 hours. The phases are then allowed to separate. The bottom aqueous phase is drained and the top organic phase containing the title compound in solution is retained for the next step. HPLC analysis indicates no detectable amount of starting ketone or E-isomer.

EXAMPLE 10

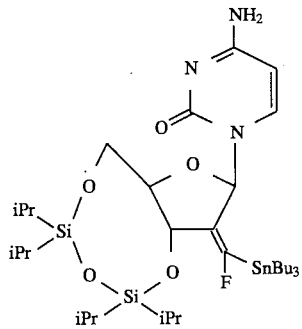

Preparation of
(Z)-2'-deoxy-2'-[fluoro(tributylstannyl)methylene]-
3',5'-O-[1,1,2,3-tetrakis(1-methylethyl)-1,3-
disiloxanediyl]-cytidine.

The above prepared solution of (Z)-2'-[fluoro(phenylsulfonyl)methylene]-3',5'-O-[1,1,3,3-tetrakis(1-methylethyl)1,3-disiloxanediyl]-cytidine (1.327 Kg) is checked with potassium iodide-starch paper to verify the absence of peroxides and is then concentrated under vacuum (35° C. to 36° C.) to provide a cloudy yellow oil that is 44% to 49% by weight of the above starting material. The material is subjected to azeotropic drying with cyclohexane at 20° C. to 40° C. and 90 to 120 torr. Approximately 9 to 11 kg of cyclohexane is used to effect the drying, affording a final cyclohexane solution that is 46% to 49% by weight of the above starting material. This solution is transferred to a 22 liter round bottomed flask. Additional cyclohexane (0.55 to 1.2 Kg) is used to rinse any cyclohexane residual to the 22 liter round bottom flask. To this solution is added tributyltin hydride (3.6 to 4.0 Kg, 2.5 to 2.7 equivalents) and azoisobutyronitrile (44 to 55 g, AIBN) at room temperature. The stirred reaction mixture is placed under nitrogen and heated to 60° C. to 65° C. The reaction mixture is allowed to stir at this temperature for 18 to 20 hours, during which time a solution of AIBN (240 to 300 g) in tetrahydrofuran (2.5 to 3.4 Kg) is added in a slow stream. The reaction mixture is cooled to room temperature and transferred to a 50 liter bottom drained flask. Tetrahydrofuran (9 to 10 Kg) is added. The resulting solution is extracted with two portions of one normal aqueous potassium hydroxide (13 to 15 Kg per extraction) and the resulting lower aqueous phases are removed from the 50 liter flask. To the product solution in the 50 liter flask is added tetrahydrofuran (4 to 5 Kg) and the resulting solution is extracted with water (13 to 15 Kg). The lower aqueous phase is removed and the product solution is concentrated under vacuum at 40° C. to 45° C. to provide the title compound as a viscous orange/brown oil (5.8 to 6.9 Kg).

EXAMPLE 11

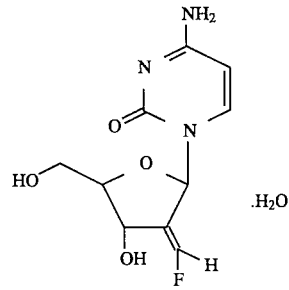

Preparation of
(E)-2'-deoxy-2'(fluoromethylene)cytidine
monohydrate

The (2'Z)-2'-deoxy-2'-[fluoro(tributylstannyl)methylene]-3',5'-O-[1,1,3,3-tetrakis(1-methylethyl)1,3-disiloxanediyl]-cytidine (6.39 Kg) prepared in example 10 is dissolved in methanol (9.24 Kg). 50% wt potassium fluoride dihydrate (4.03 Kg diluted with 1.22 Kg of water) is added with stirring. The reaction is heated to 45° C. for 48 hours. The reaction is then concentrated under vacuum at a bath temperature of 30° C. The concentrate is partitioned between water (4.0 Kg) and ethyl acetate (4.0 Kg). The lower aqueous layer is collected and saved. The upper organic layer containing tributyltin compounds and tetraisopropylsiloxyl compounds is discarded. The middle emulsion layer is filtered and the filtercake is rinsed with water (1.0 Kg) and ethyl acetate (1.0 Kg). The liltrate is allowed to separate and the lower aqueous layer is collected. The aqueous layers are then combined and rinsed with ethyl acetate (2 Kg). Diatomaceous earth (0.05 Kg) is added to the combined aqueous layers which is then vacuum filtered. The liltrate is concentrated under vacuum at a bath temperature of 30° C. Methanol (3.0 Kg) is added to the concentrate and the mixture is again concentrated under vacuum. The residue is then dissolved in methanol (5.0 Kg) and silica gel 60 (4.0 Kg, 100–200 mesh) is added. The mixture is evaporated with a continuous addition of isopropanol to maintain the original volume nearly constant. After approximately 20 Kg of distillate is collected, the slurry is added to a column containing silica gel (2.0 Kg) that has been preconditioned with isopropanol. The column is eluted with isopropanol until no product is detected in the fractions. The fractions are combined and concentrated to approximately 4 liters total volume. The slurry is filtered and the filtercake rinsed with isopropanol (1.0 Kg). The filtercake is air dried to a constant weight (0.83 Kg) to provide the crude anhydrous form of the title compound. This material is combined with similar batches and the total amount (3.82 Kg) is dissolved in water (22 Kg) and polish filtered. The liltrate is concentrated to 8–10 liters total volume under vacuum at a bath temperature of 30° C. The resulting slurry is cooled at 5° C. for 2 hours. The product is collected by vacuum filtration and rinsed with cold water (1.8 Kg). The filtercake is air dried to a constant weight (3.31 Kg, 99.8% pure by HPLC, corrected for water) to provide the title compound.

EXAMPLE 12

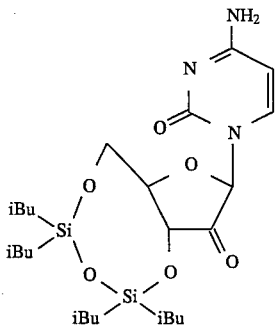

Preparation of
2'-Deoxy-2'-oxo-3',5'-O-[1,1,3,3-tetrakis(2-methyl-1-propyl)-1,3-disiloxanediyl]-cytidine The title compound can be prepared from cytidine (28.8 mol) and 1,3-dichloro-1,1,3,3-tetraisobutyldisiloxane (31.7 mol) in a manner analogous to the procedure described in example 8.

EXAMPLE 13

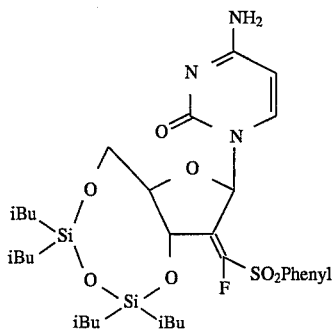

Preparation of
(Z)-2'-[fluoro(phenylsulfonyl)methylene]-3',5'-O-[1,1,3,3-tetrakis(2-methyl-1-propyl)-1,3-disiloxanediyl]-cytidine The title compound can be prepared from diethyl-1-fluoro-1-phenylsulfonylmethanephosphonate (4.483 mol) and ground 2'-Deoxy-2'-oxo-3',5'-O-[1,1,3,3-tetrakis(2-methyl-1-propyl)1,3-disiloxanediyl]-cytidine (4.266 mol) prepared in example 12, in a manner analogous to the procedure described in example 9.

EXAMPLE 14

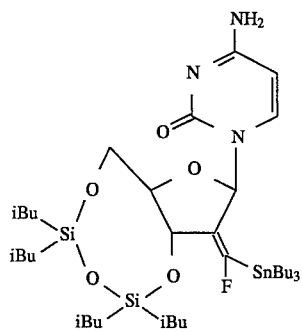

Preparation of
(Z)-2'-deoxy-2'-[fluoro(tributylstannyl)methylene]-3',5'-O-[1,1,3,3-tetrakis(2-methyl-1-propyl)-1,3-disiloxanediyl]-cytidine The title compound can be prepared from (Z)-2'-fluoro(phenylsulfonyl)methylene]-3',5'-O-[1,1,3,3-tetrakis(2-methyl-1-propyl)-1,3-disiloxanediyl]-cytidine (1.327 Kg) prepared in example 13, tributyl tin hydride (2.5 to 2.7 equivalents) and azoisobutyronitrile (44 to 55 g, AIBN) in a manner analogous to the procedure described in example 10.

EXAMPLE 15

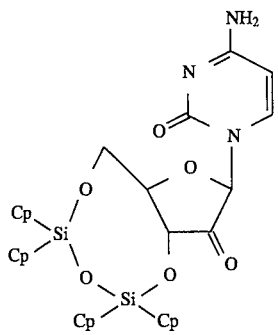

Cp represents a cyclopentyl substituent

Preparation of
2'-Deoxy-2'-oxo-3',5'-O-[1,1,3,3-tetrakis(cyclopentyl)-
1,3-disiloxanediyl]-cytidine The title compound can be prepared from cytidine (28.8 mol) and 1,3-dichloro-1,1,3,3-tetracyclopentyldisiloxane (31.7 mol) in a manner analogous to the procedure described in example 8.

EXAMPLE 16

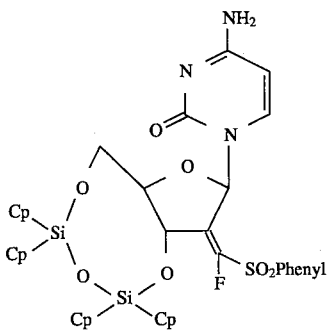

Preparation of
(Z)-2'-[fluoro(phenylsulfonyl)methylene]-3',5'-O-
[1,1,3,3-tetrakis(cyclopentyl)-1,3-disiloxanediyl]-
cytidine The title compound can be prepared from diethyl-1-fluoro-1-phenylsulfonylmethanephosphonate (4.483 mol) and ground 2'-Deoxy-2'-oxo-3',5'-O-[1,1,3,3-tetrakis(cyclopentyl)-1,3-disiloxanediyl]-cytidine (4.266 mol) prepared in example 15, in a manner analogous to the procedure described in example 9.

EXAMPLE 17

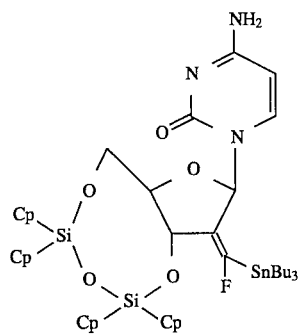

Preparation of
(Z)-2'-deoxy-2'-[fluoro(tributylstannyl)methylene]-
3',5'-O-[1,1,3,3-tetrakis(cyclopentyl)-1,3-
disiloxanediyl]-cytidine The title compound can be prepared from (Z)-2'-fluoro(phenylsulfonyl)methylene]-3',5'-O-[1,1,3,3-tetrakis(cyclopentyl)-1,3-disiloxanediyl]-cytidine (1.327 Kg) prepared in example 16, tributyl tin hydride (2.5 to 2.7 equivalents) and azoisobutyronitrile (44 to 55 g, AIBN) in a manner analogous to the procedure described in example 10.

Following the respective procedures, the anhydrous final product prepared in example 7, (E)-2'-deoxy-2'(fluoromethylene)cytidine and the monohydrate of the final product prepared in example 11, (E)-2'-deoxy-2'(fluoromethylene)cytidine monohydrate can each be prepared in an analogous manner from either (Z)-2'-deoxy-2'-[fluoro(tributylstannyl)methylene]-3',5-O-[1,1,3,3-tetrakis(2-methyl-1-propyl)-1,3-disiloxanediyl]-cytidine prepared in example 14 or (Z)-2'-deoxy-2'-fluoro(tributylstannyl)methylene]-3',5'-O-[1,1,3,3-tetrakis(cyclopentyl)-1,3-disiloxanediyl]-cytidine prepared in example 17.

What is claimed is:

1. A compound of the formula

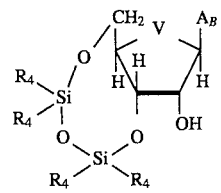

wherein

V is oxy or methylene $R_4$ is $C_2$–$C_7$ alkyl or $C_5$–$C_7$ cycloalkyl and $A_B$ is a radical of the formula

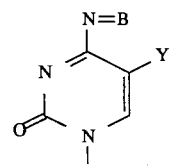

wherein Y is hydrogen, $C_1$–$C_4$ alkyl or $C_1$–$C_4$ alkoxy and B is a suitable nitrogen blocking group of the formula $CR_1NR_2R_3$ wherein $R_1$ is a hydrogen or $C_1$–$C_4$ alkyl and $R_2$ and $R_3$ are independently $C_1$–$C_4$ alkyl.

2. A compound of the formula

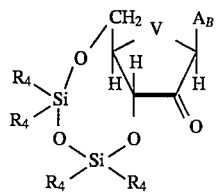

wherein
V is oxy or methylene
$R_4$ is $C_2$–$C_7$ alkyl or $C_5$–$C_7$ cycloalkyl and
$A_B$ is a radical of the formula

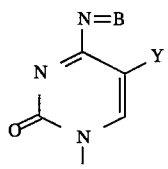

wherein Y is hydrogen, $C_1$–$C_4$ alkyl or $C_1$–$C_4$ alkoxy and B is a suitable nitrogen blocking group of the formula $CR_1NR_2R_3$ wherein $R_1$ is a hydrogen or $C_1$–$C_4$ alkyl and $R_2$ and $R_3$ are independently $C_1$–$C_4$ alkyl.

3. A compound of the formula

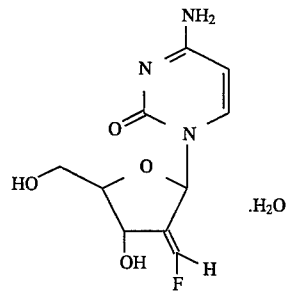

which is (E)-2'-deoxy-2'-(fluoromethylene)cytidine monohydrate.

* * * * *

UNITED STATES PATENT AND TRADEMARK OFFICE
CERTIFICATE OF CORRECTION

PATENT NO. : 5,508,393

DATED : April 16, 1996

INVENTOR(S) : James R. McCarthy, Donald P. Matthews, Jeffrey S. Sabol, Richard Donaldson It is certified that error appears in the above-indentified patent and that said Letters Patent is hereby corrected as shown below:

On the title page, item [75] "James R. McCarthy; Donald P. Matthews, both of West Chester; Jeffrey S. Sabol, Loveland, all of Ohio; James R. McConnell; Richard E. Donaldson, both of Midland, Mich.; Robert Duguid, Richmond, Va." and should read -- James R. McCarthy; Donald P. Matthews, both of West Chester; Jeffrey S. Sabol, Loveland, all of Ohio; Richard E. Donaldson, Midland, Mich.--

At column 1, line 52,       "hydrolysis" and should read --hydroxyls--.

At column 6, line 7 in the structure, the patent reads "  " and should read --  --.

At column 6, line 51,       "At" and should read --Ar--.
At column 9, line 1,        "hydrolysis" and should read --hydroxyls--.
At column 9, line 39,       "residue purified" and should read --residue is purified-- .
At column 9, line 47,       "-750°C" and should read -- -75°C-- .
At column 12, line 3,       "829" and should read --2829-- .
At column 13, line 52,      "hydrolysis" and should read --hydroxyls--.
At column 15, line 41,      "provide the the exocyclic" and should read --provide the exocyclic--.
At column 16, line 11,      "to provides" and should read --to provide--.
At column 17, line 31,      'citidine" and should read --cytidine--.
At column 17, line 50,      'flitrate" and should read --filtrate--.
At column 17, line 55,      'liltrate" and should read --filtrate--.
At column 19, line 15,      "liltrate" and should read --filtrate-- .

UNITED STATES PATENT AND TRADEMARK OFFICE
CERTIFICATE OF CORRECTION

PATENT NO. : 5,508,393

DATED : April 16, 1996

INVENTOR(S) : James R. McCarthy, Donald P. Matthews, Jeffrey S. Sabol, Richard Donaldson It is certified that error appears in the above-indentified patent and that said Letters Patent is hereby corrected as shown below:

At column 19, line 24, "(11.4 q)" and should read --(11.4 g)--.
At column 19, line 51, "0-]1," and should read --0-[1,-- .
At column 20, line 39, "4 95" and should read --4.95--.
At column 20, line 62, "of in a 1:2" and should read --in a 1:2--.
At column 22 line 9, and again at column 22, line 57, the patent reads "liltrate" and should read --filtrate--.
At column 23, line 34, "aclaea" and should read --added--.
At column 24, line 3, "[1,1,2,3-" and should read --[1,1,3,3- --.
At column 24, line 6, "methylethyl)1," and should read --methylethyl)-1-- .
At column 25, line 5, and again at line 9, the patent reads "liltrate" and should read --filtrate-- .

Signed and Sealed this

Third Day of June, 1997

*Attest:*

BRUCE LEHMAN

*Attesting Officer*  Commissioner of Patents and Trademarks